United States Patent [19]
Rampal et al.

[11] Patent Number: 5,466,351
[45] Date of Patent: Nov. 14, 1995

[54] CAPILLARY ELECTROPHORETIC SYSTEM FOR SEPARATION OF SAMPLES CONTAINING BOTH POSITIVELY AND NEGATIVELY CHARGED COMPONENTS

[75] Inventors: Sushma Rampal; Jang B. Rampal, both of Yorba Linda; James C. Osborne, Orange, all of Calif.

[73] Assignee: Beckman Instruments, Inc., Fullerton, Calif.

[21] Appl. No.: 414,684

[22] Filed: Mar. 31, 1995

[51] Int. Cl.$^6$ .......................... G01N 27/26; G01N 27/447
[52] U.S. Cl. .................................... 204/180.1; 204/182.8; 204/299 R
[58] Field of Search .............................. 204/180.1, 182.8, 204/299 R

OTHER PUBLICATIONS

K. Baechmann, I. Haumann, & T. Groh, "Simultaneous Determination of Inorganic Cations and Anions in Capillary Zone Electrophoresis (CZE) with Indirect Fluorescence Detection" Fresenius' J. Anal. Chem. 343(12), (1992), 901–2.

"Simple Apparatus for Capillary Zone Electrophoresis . . . ," by Rohlicek et al., Journ. of Chromatography, vol. 494, pp. 87–99, 1989.

"General Principles of Zone Electrophoresis," by Smith, Chromatographic & Electrophoretic Techniques, vol. II, Chapter 1, pp. 1, 56–59.

Brochure: "P/ACE™ System 2000, with Automation and Modularity for Today and Tomorrow", 8 pages. * No Month Available.

Primary Examiner—John Niebling
Assistant Examiner—John S. Starsiak, Jr.
Attorney, Agent, or Firm—William H. May; P. R. Harder; Janis C. Henry

[57] ABSTRACT

A sample having both positively and negatively charged components may be separated during the same run by injecting a plug of sample at both ends of the capillary and applying an electric field in the capillary, where there is insufficient electroosmotic flow in the capillary to reverse sample migration direction, such as in the case of a gel-filled column.

6 Claims, 4 Drawing Sheets

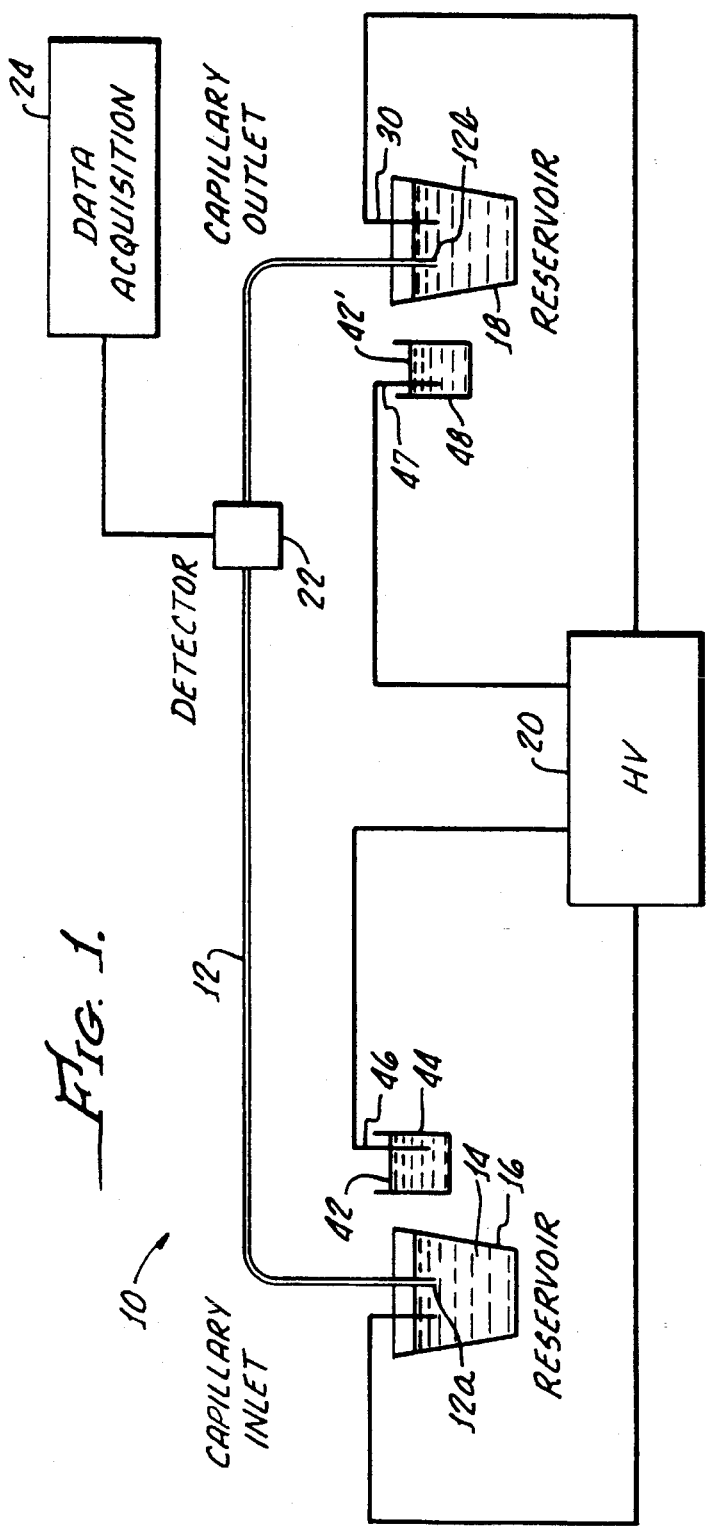
Fig. 1.
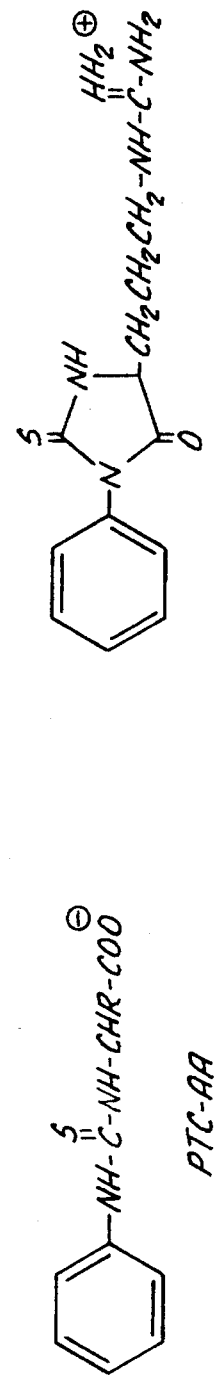
Fig. 2a. PTC-AA
Fig. 2b. PTH-Arg

CAPILLARY ELECTROPHORETIC SYSTEM FOR SEPARATION OF SAMPLES CONTAINING BOTH POSITIVELY AND NEGATIVELY CHARGED COMPONENTS

BACKGROUND OF THE INVENTION

This invention relates in general to electrophoresis and, in particular, to a capillary electrophoretic system for separating samples containing both positively and negatively charged components.

Capillary electrophoresis (CE) is emerging as one of the separation methods of choice in resolving a complex mixture into its constituents. In a typical capillary electrophoretic system, an electric field is applied across a capillary structure with typical dimensions of 2–200 microns inside diameter and 10–100 cm length. The medium is an electrolyte solution or a gel. In capillary zone electrophoresis (CZE), the capillary wall contains immobilized charges which cause the bulk solution as a whole to move under the influence of an electric field.

The above-described movement is known as electroosmotic flow. In CZE, each of the charged components of the sample also has electrophoretic mobility and components with different mobilities would migrate at different rates. Even though a sample may contain both positively and negatively charged components, since the electroosmotic flow rate is typically higher than the electrophoretic mobilities of most components, usually both positively charged and negatively charged components will be caused to move in the same direction when carried by the electroosmotic flow.

Where there is little or no electroosmotic flow in the capillary, it may be difficult in the conventional electrophoretic scheme to cause both positively charged and negatively charged components to migrate past the detector. For example, if a sample containing both negatively charged and positively charged components is injected into a gel-filled capillary at its cathodic end, the negatively charged components will migrate towards the anodic end of the capillary whereas the positively charged components will remain essentially at the cathodic end and fail to move. If the sample is injected at the anodic end of the gel-filled capillary, then the positively charged components of the sample will migrate towards the cathodic end and separate in the process while the negatively charged components will remain essentially at the anodic end and fail to move. The above is true also for separations using capillaries with treated inner walls to reduce or eliminate electroosmotic flow.

Since samples to be analyzed frequently do include both positively and negatively charged components, it is therefore desirable to provide a system that can be used to separate both positively charged and negatively charged components in a single run. None of the existing conventional electrophoretic systems is entirely satisfactory for solving this problem. It is therefore desirable to provide an improved electrophoretic system as a solution.

SUMMARY OF THE INVENTION

The invention is based on the observation that by injecting two portions of a sample, one at the anodic end and the other at the cathodic end of the capillary, the positively charged components of sample injected at the anodic end will migrate towards the cathodic end and separate and the negatively charged components of the portion injected at the cathodic end of the capillary will migrate towards the anodic end and separate, so that both positively and negatively charged components of the sample will be caused to separate in the same run. If a first sample is injected into the capillary at one end and a second sample is injected at the other end, then the positively charged components of one sample will migrate and separate and the negatively charged components of the other sample will also migrate and separate during the same electrophoretic run.

Therefore, one aspect of the invention is directed towards an electrophoretic method comprising the step of providing a capillary having a first and a second opening that are spaced apart from each other, said capillary containing an electrolyte between the two openings, introducing a first sample into the capillary through the first opening and a second sample through the second opening, and applying an electric field gradient in the electrolyte between the two openings to cause the two samples or portions thereof to migrate into the capillary in opposite migration directions and to separate into components, wherein an electroosmotic flow present between the two openings, if any, is such that it will not overcome the effect of the electric field gradient so as to cause a reversal of migration direction of the two samples or portions thereof. While the two openings can be at the two ends of the capillary, this is not required for the operation of the invention.

BRIEF DESCRIPTION OF THE DRAWINGS

FIG. 1 is a schematic diagram of a capillary electrophoretic system to illustrate the invention.

FIG. 2a shows the chemical structure of PTC-AA's which are negatively charged in water or in basic buffers used for electrophoretic separation.

FIG. 2b shows the chemical structure of PTH-Arg which is positively charged in water or in basic buffers used for electrophoretic separation.

DETAILED DESCRIPTION OF THE PREFERRED EMBODIMENT

Figure 3:
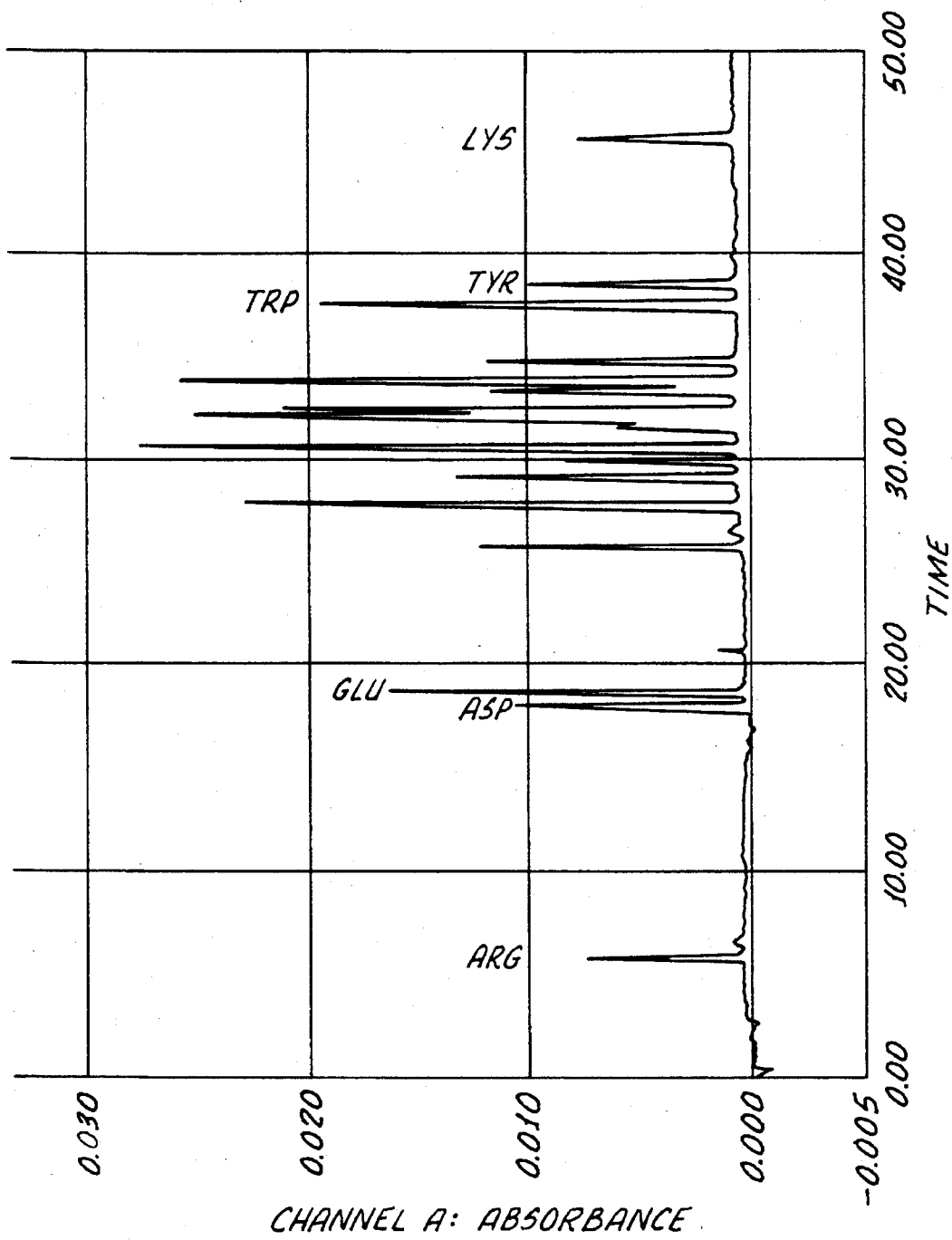
FIGS. 3, 4 and 5 are electropherograms illustrating the results of the separation employing the apparatus of FIG. 1 and the derivatized amino acids of FIG. 2.

FIG. 1 is a schematic diagram of a capillary electrophoretic system illustrating the preferred embodiment of the invention. As shown in FIG. 1, system 10 includes a capillary 12 with two openings one at each end of the two ends 12a, 12b of the capillary. End 12a of the capillary is in contact with an electrolyte 14 contained in the reservoir 16 and end 12b is in contact with an electrolyte in reservoir 18. Capillary 12 is filled with a solid phase such as a gel electrolyte. Alternatively, the inner wall of capillary 12 may be coated with a material in a manner known to those skilled in the art to reduce or eliminate electroosmotic flow when a high voltage is applied across the electrolytes in the reservoirs 16, 18. An electrical potential difference is established between reservoirs 16 and 18. As shown in FIG. 1, the potential difference may be established by means of a high voltage supply 20 and electrodes such as 30 submerged in the reservoir electrolytes. The separated components are detected by detector 22 placed at a position along capillary 12. Detector 22 provides an output signal to data acquisition unit 24 for analyzing the signal to provide useful information, such as in the form of an electropherogram.

In conventional capillary electrophoresis, the sample to be analyzed and detected is introduced into one end of the capillary, such as through the opening at end 12a by dipping end 12a briefly into a sample solution 42 in a container or vial 44 and an electrical potential difference applied between sample solution 42 and reservoir 18 by means of electrodes 30 and 46. A plug of sample 42 is then electrokinetically injected into the opening at end 12a of the capillary. End 12a of the capillary is then withdrawn from solution 42 and placed in the electrolyte solution 14 in reservoir 16. The high voltage supply 20 then applies the high voltage between reservoirs 16 and 18, causing the plug of sample introduced into the capillary to migrate towards end 12b and separate into its components. Detector 22 then detects the separated component and the data acquisition unit 24 processes the output signal of the detector to provide an electropherogram.

In the above-described process, where there is insignificant electroosmotic flow in capillary 12, and if the plug of sample 42 contains both positively and negatively charged components, then the above process can separate and detect only the components of either the positively charged type or the negatively charged type, but not both. Thus, if electrolyte 14 is at a lower electrical potential compared to the electrolyte in reservoir 18, then only the negatively charged components will migrate towards end 12b, and will separate and be detected. The above process frequently does not adequately resolve the positively charged components.

According to the teachings of the invention, prior to, or after, or while the plug of sample 42 is injected into the opening at end 12a of the capillary, a second plug of sample 42' is injected into end 12b of the capillary, also by dipping end 12b into sample solution 42' in reservoir 48 by means of electrokinetic injection using high voltage 20 and electrode 47. End 12b is then dipped into the electrolyte in reservoir 18. Thus, when high voltage 20 applies a voltage to cause reservoir 16 to be at a lower electrical potential than reservoir 18, the positively charged components of the plug of sample 42' will migrate from end 12b through the capillary 12 towards end 12a of the capillary. If the plug of sample 42 and the plug of sample 42' contain the same sample components, the negatively charged components (common to the two samples) of the plug from sample 42 will migrate from end 12a towards end 12b while the positively charged components (also common to the two samples) of the plug from sample 42' will migrate in the opposite direction, thereby separating and detecting both types of components in the same process or run. It is of course possible to analyze two different types of samples if samples 42, 42' contain different sample components. While in the embodiment of FIG. 1, the two openings of the capillary 12 through which samples introduced are shown at the two ends of the capillary, it will be understood that this is not required and the invention described above will function in the same way even if the two openings are at two different intermediate locations of the capillary away from the ends of the capillary, where the above-described separation process would then occur in a section of the capillary between the two openings.

If a sample contains more negatively charged components than positively charged components, it may be desirable in the above-described scheme of FIG. 1 to place the detector 22 at a position along capillary 12 that is closer to the anodic opening than the cathodic opening, where the anodic opening of the capillary is defined as the one at a higher electrical potential than the other opening referred to as the cathodic opening. Thus, if reservoir 16 is at a lower electrical potential than reservoir 18, and the sample contains more negatively charged components than positively charged components, then it is preferable for detector 22 to be placed at a position along capillary 12 that is closer to end 12b than to end 12a. This will allow the many negatively charged components to migrate and separate along the longer section of the capillary between detector 22 and end 12a and the fewer positively charged components to migrate and separate into the shorter section of the capillary between detector 22 and end 12b.

While the capillary 12 is described above as being filled with gel or treated by coating its inner walls to reduce or eliminate electroosmotic flow, the invention will function as described above even if electroosmotic flow is present, if any electroosmotic flow present between the two openings is such that it will not overcome the effect of the electric field gradient so as to cause a reversal of migration direction of the two samples or portions thereof. The electric field gradient will urge some sample components to move in a direction opposite to that of the electroosmotic flow. If the electroosmotic flow rate is high enough to overcome the effect of the gradient, then such components will be caused by the flow to move in the same direction as the flow. Then the two samples injected at opposite ends of the capillary will move in the same direction and the advantages of this invention will not be achieved. Thus the advantages of this invention are obtained when the electroosmotic flow rate is less than the electrophoretic migration rates of sample components that are otherwise migrating under the influence of the gradient in a direction opposite to that of the electroosmotic flow. In such event, such sample components will still migrate in the same direction as they would have if electroosmotic flow is not present, but at rates given by the difference between their electrophoretic migration rates and the electroosmotic flow rate.

In one experiment using system 10 of FIG. 1, a mixture of negatively charged phenylthiocarbamyl amino acids (PTC-AA) and positively charged phenylthiohydantoin-Arginine (PTH-Arg) was analyzed in accordance with the present invention. The PTC-AA's have the general structure shown in FIG. 2a and PTH-Arg has the structure shown in FIG. 2b. The mixture was injected into the openings at the cathodic end and the anodic end of a gel-filled capillary having a length of 47 cm, an inner diameter of 100 μm and a detector 22 located 40 cm from the cathodic end. A standard borate buffer was the running electrolyte filling reservoirs 16 and 18 and the capillary gel was 3% T (wt % polyacrylamide in the gel composition). The result of the analysis is illustrated in the electropherogram of FIG. 3. The positively charged PTH-Arg migrated toward the cathodic opening and because it passed the detector window first in time after being injected at the anodic end, it is observed early in the electropherogram. The negatively charged PTC-AA's migrated toward the anodic opening of the capillary and where observed later in the electropherogram.

Figure 4:
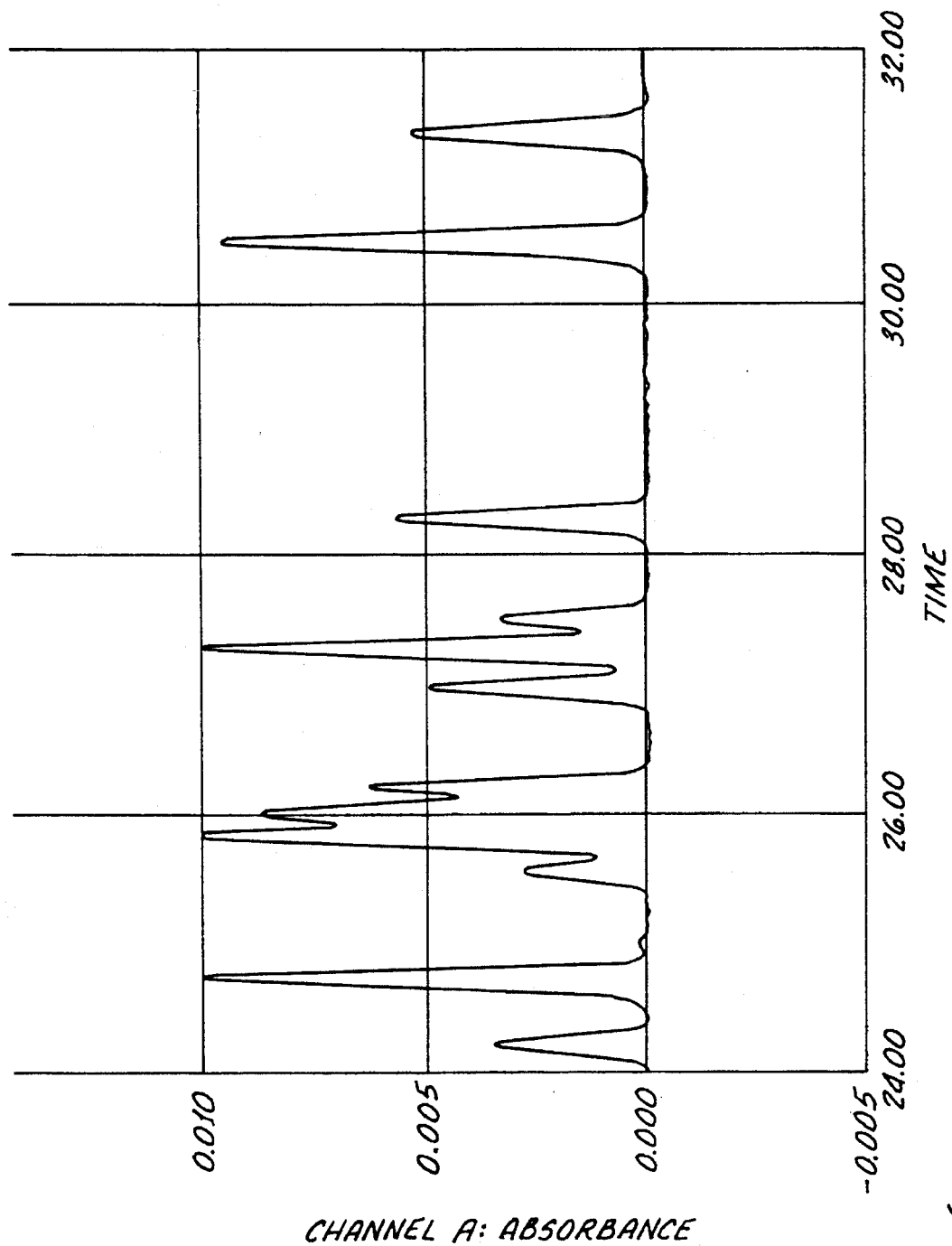
Figure 5:
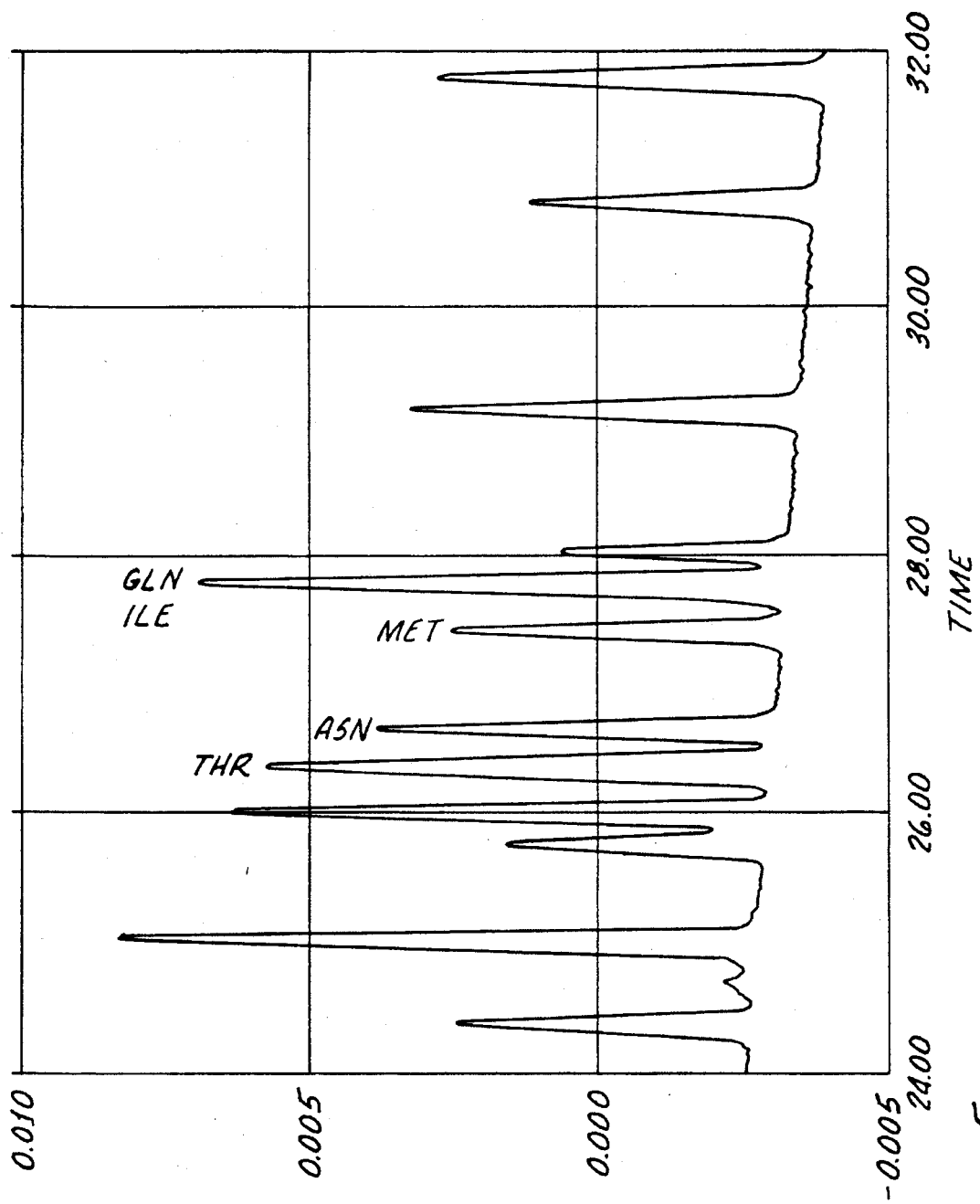

The analysis of the PTC-AA's and PTH-Arg was repeated using capillary gels of different compositions. The electropherogram illustrated in FIG. 4 was obtained using a 10% T gel and shows improved resolution over the electropherogram of FIG. 3 obtained under the same conditions. The electropherogram of FIG. 5 was obtained using a gel column prepared with 15% T and gave well-resolved peaks clearly indicating the PTC-AA's and PTH-Arg. The high resolution seems to be the result of the sieving properties of the gel. The dual injection technique described above in reference to FIG. 1 and appropriate composition of the gel could be useful in peptide and protein sequencing in the analysis of other charged molecules.

While the invention has been described above by reference to various embodiments, it will be understood that different variations and modifications may be made without departing from the scope of the invention which is to be limited only by the appended claims. For example, instead of using gel-filled columns in systems 10 and 100, it is possible to reduce or eliminate electroosmotic flow in the capillaries by treating the inner walls of the capillaries in a manner known to those skilled in the art to accomplish the same purpose.

What is claimed is:

1. An electrophoretic method comprising the steps of:

providing a capillary having a first and a second opening that are spaced apart from each other, said capillary containing an electrolyte between the two openings;

introducing a first sample into the capillary through the first opening and a second sample through the second opening; and applying an electric field gradient in the electrolyte between the two openings to cause the two samples to migrate in the capillary in opposite directions and to separate into components, wherein an electroosmotic flow, if any, present between the two openings is such that it will not overcome the effect of the electric field gradient so as to cause a reversal of migration direction of the two samples or portions thereof.

2. The method of claim 1, wherein said applying step applies a first electrical potential to the electrolyte through the first opening and a second electrical potential to the electrolyte through the second opening, the second potential being higher than the first potential, so that positively charged components of the samples migrate from the second opening towards the first opening and negatively charged components of the sample migrate from the first opening towards the second opening.

3. The method of claim 2, further comprising the step of detecting the separated sample components in the capillary at a position along the capillary.

4. The method of claim 3, further comprising selecting the position such that when the sample contains more positively charged components than negatively charged components, the position is selected to be closer to the first opening than to the second opening, and when the sample contains more negatively charged components than positively charged components, the position is selected to be closer to the second opening than to the first opening.

5. The method of claim 1, wherein said introducing step includes injecting by pressure difference or electrokinetic injection.

6. The method of claim 1, wherein said providing step provides a capillary containing a gel electrolyte.

\* \* \* \* \*